United States Patent [19]

McDaniel

[11] Patent Number: 5,443,844
[45] Date of Patent: Aug. 22, 1995

[54] LINOLEIC ACID PREPARATIONS FOR TOPICAL TREATMENT OF ACNE VULGARIS

[76] Inventor: William R. McDaniel, 9158 Saddlebow Dr., Brentwood, Tenn. 37027

[21] Appl. No.: 187,138

[22] Filed: Jan. 27, 1994

Related U.S. Application Data

[63] Continuation of Ser. No. 985,103, Dec. 3, 1992, abandoned.

[51] Int. Cl.$^6$ .......................... A61K 7/48; A61K 7/00
[52] U.S. Cl. ..................................... 424/484; 424/490; 424/401; 514/859; 514/558; 514/560
[58] Field of Search ....................... 424/401, 484, 489; 514/859

[56] References Cited

U.S. PATENT DOCUMENTS

| | | | |
|---|---|---|---|
| 4,309,415 | 1/1982 | Horrobin | 424/643 |
| 4,444,755 | 4/1984 | Horrobin | 424/642 |
| 4,699,924 | 10/1987 | Durrant | 514/738 |
| 4,710,383 | 12/1987 | Dick | 424/449 |
| 4,740,432 | 4/1988 | Bosserelle | 424/59 |
| 4,837,026 | 5/1989 | Rajakhyaksha | 514/788 |
| 5,231,087 | 7/1993 | Thornfedlt | 514/53 |

Primary Examiner—Thurman K. Page
Assistant Examiner—Sally Gardner

[57] ABSTRACT

A preparation for topical application of linoleic acid, for treatment of acne, and *Propionibacteriem acnes*, contains between about 0.1% and about 10%, preferably between about 1% and about 5% and specifically about 2% of linoleic acid. This acts both as an antibiotic and as a means for correcting the essential fatty acid imbalance in sebum which causes follicular plugging and triggers the process.

4 Claims, No Drawings

LINOLEIC ACID PREPARATIONS FOR TOPICAL TREATMENT OF ACNE VULGARIS

This application is a continuation of Ser. No. 07/985,103, filed Dec. 3, 1992 now abandoned.

This invention relates to Linoleic Acid preparations for topical application, and in particular for treatment of Acne Vulgaris.

Fatty acids are the building blocks from which all lipid materials in the human body are made. While the human diet provides a constant source of fatty acids, most are also able to be synthesized in the body through various chemical reactions that lengthen or shorten the carbon chain or alter the chemical bond structure. Only three fatty acids (linoleic, linolenic, and arachidonic) are unable to be made in vivo and must therefore be obtained from dietary sources. These fatty acids are thus referred to as essential fatty acids. Linoleic acid is the most important: it has been shown to correct most signs of clinical essential fatty acid (EFA) deficiency whereas linolenic acid and arachidonic acid cannot.

Structurally, fatty acids are long-chain molecules with varying numbers of carbon atoms and varying degrees of saturation of the chemical bonds. They are chemically described by three numbers: the number of carbon atoms in the chain, the number of double bonds, and the number of carbon atoms between the terminal unsaturated bond and the methyl end of the fatty acid (the omega number). Linoleic acid by this system of nomenclature is 18:2 omega 6, meaning 18 carbon atoms, two double bonds, and six carbon atoms between the terminal unsaturated bond and the methyl end.

Essential fatty acids have long been known to have significance in humans and human disease states. Many reports describing patients in whom dietary lack of EFA resulted in pathologic states have appeared in the medical literature. Most information has come from patients receiving total parenteral nutrition for extended periods who were not given adequate quantities of EFA in their intravenous fluids. The most prominent finding in these patients has been a chronic scaly dermatosis with increased skin water loss due to loss of an intact skin barrier. Also noted are thickening of the epidermis and the keratin layer, an indication of altered keratinization. Sebaceous glands diminish markedly in size. Patients are noted to develop brittle hair and to lose hair from the scalp and eyebrows but have not been reported to get acne in the total deficiency state. Absorption of topically applied linoleic acid proved adequate to correct this systemic condition in several cases.

One of the most accessible lipid materials for evaluation in the body is sebum, which is produced by skin appendages known as sebaceous glands. These glands are noted in most areas of the body having hair follicles but are much larger in size and much more active in secretion on the face and scalp. Sebum is made up of triglycerides (57%), wax esters (26%), and squalene (12%), with a very small amount of cholesterol and cholesterol esters. Both triglycerides and wax esters are composed of fatty acids. Therefore a dietary deficiency or any other method of depleting the essential fatty acids would be expected to significantly affect the production of sebum. Indeed, combined deficiency of all EFA results in diminished sebum production and decreased sebaceous gland size. Sebum plays a prominent role in the human condition of particular concern in the present invention, acne vulgaris.

Acne is a chronic, inflammatory and often disfiguring condition affecting primarily the face, neck, and upper trunk of post-pubertal men and women. The pathogenesis involves initial plugging of follicular structures due to altered keratinization of the follicular epithelium. After this, the bacterium *Propionibacteriem acnes* increases in number in the follicles and results in hydrolysis of sebaceous triglycerides and wax esters into free fatty acids and glycerol. Free fatty acids inflame the follicular epithelium and rupture follicles, setting off a cascade of inflammatory reactions which eventuate in the lesions seen clinically as acne papules, pustules and cysts. Downing et al were the first to show that the rapid sebaceous secretion seen in acne patients created a state of localized linoleic acid deficiency in the sebaceous gland.[1] These glands produce linoleic acid-depleted sebum which they postulated could alter follicular keratinization and initiate acne lesions. This theory got substantially more credibility when Strauss et al evaluated the linoleic acid levels in sebum from patients treated for acne with oral 13-Cis retinoic acid.[2] This medication, the most effective acne treatment ever discovered, dramatically reduces sebum secretion and sebaceous gland size during the treatment period. Interestingly, when the volume of sebum secretion lessened, the percentage of linoleic acid which was low before therapy was noted to increase dramatically but fell again to pretreatment levels after the drug was stopped and sebum secretion again increased. The clinical response in the disease appeared to parallel the increase in the sebum linoleic acid concentration.

Downing, Donald P. PhD, et al., "Essential Fatty Acids and Acne", *Journal of American Academy of Dermatology*, Vol. 14 (#2, part 1), pp. 221–225, 1986.

Strauss, John S., MD, et al., "The Effect of 13-Cis-Retinoic Acid on Sebaceous Glands", *Archives of Dermatology*, Vol. 123, pp. 1538–4, 1987.

However, there is considerable expense and potential risk of treatment with oral 13-Cis retinoic acid. The drawbacks of this medication, especially its teratogenic effects on pregnant female patients, make it an unacceptable method of chronic suppression of the acne process.

The present invention concerns the treatment of acne vulgaris by the topical application of linoleic acid preparations, as exemplified by examples.

Heretofore, it has not been considered that the acne process could be treated by direct local application of linoleic acid to the affected skin areas, although penetration into the skin could reasonably be expected.

Through studies just completed, it has been found that linoleic acid, both when incorporated into growth media and when applied in serial concentrations to discs on the surface of plated bacterial cultures, acts as a very effective antibiotic against two strains of *Propionibacterium acnes* (strains 6919 and 25746) which have been cultured from lesions of acne. The effect was seen to increase in direct proportion to the concentration of linoleic acid. Nearly total inhibition of bacterial growth was achieved at a concentration of 2% (by volume) linoleic acid. Linoleic acid, when applied topically, by correcting the localized EFA deficiency seen in acne would also be expected to reduce comedo (whitehead or blackhead) formation, which, as mentioned, is due to altered keratinization.

Tables 1 and 2 illustrate the effectiveness of the topical application of linoleic acid.

TABLE 1

INHIBITION OF P. acnes GROWTH BY LINOLEIC ACID IN DISCS: EFFECTS OF CULTURE AGE AND DENSITY

| Isolate | Linoleic Concentration (%)[a] | Serial Dilutions[b] 1/100 24-hr. | 5-day | 1/1000 24-hr. |
|---|---|---|---|---|
| 6919 | 0 | 13[c] | 13 | 13 |
|  | 0.1 | 15 | —[d] | 15 |
|  | 0.25 | 17 | — | 17 |
|  | 0.5 | 18 | 13.5 | 20 |
|  | 0.75 | 19 | — | 20 |
|  | 1.0 | 20 | 14 | 21 |
|  | 2.0 | — | 15 | — |
|  | 4.0 | — | 16 | — |
| 25746 | 0 | 13 | 13 | 13 |
|  | 0.1 | 14 | — | 16 |
|  | 0.25 | 15 | — | 18 |
|  | 0.5 | 17 | 14 | 20 |
|  | 0.75 | 19 | — | 21 |
|  | 1.0 | 20 | 15 | 22 |
|  | 2.0 | — | 17 | — |
|  | 4.0 | — | 18 | — |

[a]25 μl/disc.
[b]Serial dilutions from either 24-hour or 5-day starter cultures using 1% peptone - 0.85% NaCl. One serial dilution (1/100) made from 5-day starter cultures.
[c]Disc diameter = 13 mm; average diameter of 2 different discs from 24-hour cultures and 6 different discs from 5-day cultures.
[d]Not determined.

TABLE 2

EFFECTS OF LINOLEIC ACID IN AGAR MEDIA UPON CELL VIABILITY

| Isolate | Age of Culture[a] | Linoleic Concentration (%)[b] | Number of Viable Cells/ml |
|---|---|---|---|
| 6919 | 48 hr. | 0 | 252,000,000 |
|  |  | 0.5 | 20,400,000 |
|  |  | 1.0 | 1,500,000 |
|  |  | 2.0 | 2,300 |
|  |  | 4.0 | NG[c] |
|  | 5 Day | 0 | 29,000,000 |
|  |  | 0.5 | 5,200,000 |
|  |  | 1.0 | 340,000 |
|  |  | 2.0 | 3,800 |
|  |  | 4.0 | NG |
| 25746 | 48 hr. | 0 | 76,000,000 |
|  |  | 0.5 | 710,000 |
|  |  | 1.0 | 8,200 |
|  |  | 2.0 | NG |
|  |  | 4.0 | NG |
|  | 5 Day | 0 | 22,700,000 |
|  |  | 0.5 | 590,000 |
|  |  | 1.0 | 3,700 |
|  |  | 2.0 | NG |
|  |  | 4.0 | NG |

[a]Age of starter cultures from which serial dilutions were prepared.
[b]Final % concentration present in agar.
[c]NG = no visible growth at lowest serial dilution (1/100).

Linoleic acid therefore acts both to prevent abnormal keratinization and as an antibiotic against P. acnes.

Initial paired comparison studies with a 2% linoleic acid composition compared with the lotion base alone have shown promising effects in lessening acne lesions. Patient tolerance of the compound has been good and side effects negligible. The product is effective in various carrier vehicles, and varying concentrations can be used.

Linoleic acid is effective over a range of concentrations for example from just above zero, for example 0.1%, up to 10% or more. It is unlikely that concentration above 10% will show any advantages and concentrations between 1% and 10% are satisfactory, or even between 1% and about 5%. A preferred concentration is about 2%, because as shown above, the antibacterial effect approaches its peak at that level, and higher levels add more oiliness to the consistency of the product.

It is applied, as an example, twice a day, applying about 1 cc, although to some extent the amount will depend on the area of attack. The length of treatment will vary and in severe cases continuous treatment for months may be needed.

The linoleic acid can be combined with various bases, such as an astringent vehicle, a lotion, a cream, an oil and also be in a microencapsulated form in which microdroplets of linoleic acid are prepared in a process that surrounds them with a film of lecithin molecules for added penetration and water solubility.

What is claimed is:

1. A method of treating human skin against Propionibacterium acnes, comprising applying directly to the affected skin linoleic acid in a carrier vehicle, the linoleic acid having a concentration of about 0.1% to about 10% by volume.

2. The method of claim 1, the linoleic acid having a concentration of about 1% to about 5% by volume.

3. The method of claim 1, including applying the linoleic acid and carrier in the amount of at least abut 1 cc, about twice a day.

4. The method of claim 1, where the linoleic acid is applied directly to areas of skin affected by acne vulgaris to achieve the therapeutic effect of reduction of inflammation caused by Propionibacterium acnes-induced lipolysis of triglycerides into free fatty acids.

* * * * *